(12) United States Patent  
Haas et al.

(10) Patent No.: US 8,475,717 B2  
(45) Date of Patent: Jul. 2, 2013

(54) EXPLOSIVE OR DRUG DETECTION REPORTING SYSTEM

(75) Inventors: Jeffrey Haas, San Ramon, CA (US); Douglas Haas, Lancaster, CA (US)

(73) Assignee: Chemspectra, Inc., Pleasanton, CA (US)

( * ) Notice: Subject to any disclaimer, the term of this patent is extended or adjusted under 35 U.S.C. 154(b) by 833 days.

(21) Appl. No.: 12/498,562

(22) Filed: Jul. 7, 2009

(65) Prior Publication Data

US 2012/0176498 A1   Jul. 12, 2012

(51) Int. Cl.
*G01J 1/48* (2006.01)

(52) U.S. Cl.
USPC ............... 422/87; 422/68.1; 422/83; 422/86; 422/403; 436/46; 436/164; 436/166; 436/171

(58) Field of Classification Search
USPC ............... 73/35.14; 422/87, 68.1, 50, 78–80, 422/83, 86, 400, 402, 403; 436/43, 46, 106–107, 436/110, 127, 135, 164–166, 171, 172
See application file for complete search history.

(56) References Cited

U.S. PATENT DOCUMENTS

| | | | |
|---|---|---|---|
| 5,109,691 A | 5/1992 | Corrigan | |
| 5,296,380 A | 3/1994 | Margalit | |
| 5,455,606 A | 10/1995 | Keeling | |
| 5,644,341 A | 7/1997 | Fujii | |
| 5,648,047 A | 7/1997 | Kardish | |
| 6,518,068 B1 * | 2/2003 | Gambini et al. | 436/50 |
| 7,368,292 B2 | 5/2008 | Hummel | |
| 7,605,367 B2 | 10/2009 | Miller | |
| 7,666,684 B2 | 2/2010 | Swager | |
| 7,834,320 B2 * | 11/2010 | Goldberg et al. | 250/370.01 |
| 7,867,445 B1 * | 1/2011 | Haas et al. | 422/68.1 |
| 8,071,385 B2 * | 12/2011 | Haas et al. | 436/50 |
| 8,088,332 B2 * | 1/2012 | Haas et al. | 422/68.1 |
| 8,252,602 B2 * | 8/2012 | Haas | 436/169 |
| 8,304,251 B2 * | 11/2012 | Haas et al. | 436/107 |
| 2005/0101027 A1 * | 5/2005 | Haas | 436/109 |
| 2009/0246881 A1 * | 10/2009 | Toal et al. | 436/110 |
| 2010/0184229 A1 * | 7/2010 | Haas et al. | 436/50 |
| 2011/0102564 A1 * | 5/2011 | Haas et al. | 348/61 |
| 2012/0094387 A1 * | 4/2012 | Haas et al. | 436/43 |

OTHER PUBLICATIONS

Manual for ChemSpectra Ex-DetectTM, Mini XD-2, Oct. 2009.
Manual for KeTech Spectrex SPX 300 Trace Explosives Detector, Date Unknown.
Manual for Spectrex Ex-Detect TM, Model XD-2 Explosives Detector, Mar. 2007.

* cited by examiner

*Primary Examiner* — Hezron E Williams
*Assistant Examiner* — Hoang Nguyen
(74) *Attorney, Agent, or Firm* — Tran & Associates (57) ABSTRACT

A police tester to detect the presence of a target substance includes a housing adapted to be mounted in a police cruiser; a chemical reservoir insertable into the housing; a test swipe in a disc or an automated cartridge, the test swipe adapted to receive a chemical from the chemical reservoir, the test swipe including one or more chemically treated pads; a camera to capture an image from the test swipe; a processor coupled to the camera to process the image to detect the target substance; and a transmitter coupled to the processor to transmit a test result to a remote computer at a police headquarter.

20 Claims, 7 Drawing Sheets

EXPLOSIVE OR DRUG DETECTION REPORTING SYSTEM

BACKGROUND

This invention relates to systems for the detection of explosives and other controlled substances such as drugs or narcotics as well as other chemicals used in clandestine activities.

Recent terror attacks have changed the dynamics of the explosive detection systems across the globe. Terrorists, acting singly or in concert, instill immense fear and apprehension in civilians and governments alike with their technical knowledge about explosives. In parallel, the world has experienced an increase in the transportation of contraband substances such as drugs or narcotics.

However, the field drug tests used by police around the country are wildly inaccurate leading to false arrests. According to a Dallas criminal defense lawyer at http://www.dallascriminaldefenselawyerblog.com/2009/03/police_field_drug_tests_garbag.html, there were over 500 cases over a two year period in Dallas county in which a suspected was arrested for drug possession and lab tests proved the substance was not drugs. Due to the significant implications of a false positive (an arrest based on wrong drug test result) or the possibility that a suspect with explosives or contraband substance is not detected by the field drug test, a reliable field drug tester is needed.

SUMMARY

In one aspect, a police tester to detect the presence of a target substance includes a housing adapted to be mounted in a police cruiser; a chemical reservoir insertable into the housing; a test swipe in a disc or an automated cartridge, the test swipe adapted to receive a chemical from the chemical reservoir, the test swipe including one or more chemically treated pads; a camera to capture an image from the test swipe; a processor coupled to the camera to process the image to detect the target substance; and a transmitter coupled to the processor to transmit a test result to a remote computer at a police headquarter.

Implementations of the above aspect may include one or more of the following. The chemically treated pad can be a substantially round shape. A sequence of one or more chemicals can be delivered to the pad to detect an explosive compound. Each chemical causes the pad to display a color unique to the explosive compound. The sequence of chemicals are deposited onto the pad at predetermined times. The sequence of chemicals is deposited onto the pad at predetermined temperature range(s). The sequence of chemicals is deposited onto the pad at predetermined hold time(s) each at predetermined temperature range(s). Each chemical deposited under predetermined time and temperature conditions reacts to a specific explosive or class of explosives to yield a specific color unique to that explosive. The color is interpreted by the algorithms at specific times, temperature and chemistry to identify or characterize the explosive or class of explosives. The chemically treated pad can be a substantially round shape and adapted to receive a sequence of one or more chemicals to detect an explosive compound. The base can have a dull black color. The pad region can be a cloth with an ink free border.

The chemically treated pad can also be a substantially four-sided shape with a plurality of pads. One or more chemicals can be deposited onto the respective pads to detect one or more drug compounds. Each chemical causes the pad to display a color unique to the drug compound. The sequence of chemicals are deposited onto their respective pads at predetermined times. The sequence of chemicals is deposited onto the pad at predetermined temperature range(s). The sequence of chemicals is deposited onto the pad at predetermined hold time(s) each at predetermined temperature range(s). Each chemical deposited under predetermined time and temperature conditions reacts to a specific drug to yield a specific color unique to that drug. The chemically treated pad can be a substantially four-sided shape and adapted to receive a sequence of one or more chemicals to detect a drug compound. The chemically treated area can have a plurality of test regions. A plurality of unique chemical solutions can be deposited on each test region generating a unique color of the respective pad. The pads collectively generate a unique color pattern or code for a particular drug or class of drugs. The chemical solutions can be deposited separately or at same time to the respective test regions on the swipe. The base can have a dull black color. The pad region can be a cloth positioned on a zone of the base that is white in color with an inert ink free border.

In another aspect, a method to analyze a swiped sample to identify a chemical composition, includes clamping a test swipe under a camera and above a heater, the test swipe having a base; a chemically treated pad containing the swiped sample positioned above the base; and a tab attached to one side of the base; actuating a piezoelectric transducer that deposits a series of chemical solution agents into the swiped sample without dripping so that the device may be held at any angle of position or orientation; heating the swiped sample to one or more predetermined temperatures at a controlled rate and hold times to optimize and accelerate the chemical reactions; capturing one or more images of the chemical reaction; sending the images to the a display screen for operator observation; and analyzing the images to identify the chemical composition based on a chemical reaction and sequence of occurrence and database.

In another aspect, a system is disclosed to remotely and automatically collect sample particles by air filtration on a series of swipes at under remote control or any pre-set, pre-determined time. The system can analyze any or all swipes on command to identify a chemical composition collected according to date and time. In one embodiment, the system includes a series of pre-loaded swipes in a cartridge whereby the test swipes are clamped in the holder, rotated in and out of a air filtration position for any period of time controlled by the operator, and the test swipes may then be rotated under a camera and above a heater. The test swipe can have a base; a chemically treated pad containing the swiped sample positioned above the base; and a tab attached to one side of the base. The system can actuate a piezoelectric transducer or pumps that deposits a series of chemical solution agents into the swiped sample without dripping so that the device may be held at any angle of position or orientation; heating the swiped sample to one or more predetermined temperatures at a controlled rate and hold times to optimize and accelerate the chemical reactions. The system then captures one or more images of the chemical reaction; sends the images to the a display screen for operator observation; and analyzes the images to identify the chemical composition based on a chemical reaction and sequence of occurrence and database.

In yet another aspect, a portable handheld chemical analytical apparatus that analyzes a test swipe for chemicals such as household, drug, and clandestine, and explosive chemicals is disclosed. The apparatus includes a heater to warm the test swipe to a predetermined temperature; a clamp to secure the test swipe to the heater; one or more piezoelectric actuators connected to a chemical reservoir to dispense one or more chemicals onto the test swipe; a fan to circulate chemical vapors rising from the test swipe; and a camera to capture an image of the test swipe for analysis.

In another aspect, a method to analyze a swiped sample to identify a chemical composition, includes dispensing a series of chemical solution agents into the swiped sample; heating the swiped sample to one or more predetermined temperatures at a controlled rate to accelerate and optimize the chemical reactions or a series of chemical reactions reproducibly; capturing one or more images of the chemical reaction; sending the images to the display screen for operator observation; and analyzing the images electronically to identify the chemical composition in an unbiased fashion based on a chemical reaction database.

Advantages of the system may include one or more of the following. The system can determine quickly and reliably dangerous containers. The system tests the presence of chemical materials or compounds using a number of factors or parameters singly or in concert. The factors can include heat, volume, time, temperature, and vapor control, among others and sequences these factors over time. The sequences can be in unique intervals. As a result, the system produces highly reliable color results from specific reaction chemistry under the controlled parameters and reduces "false positives" due to its multi-factor, multi-step diagnostic operations.

The device is accurate, can operate in any orientation, requires low power, and is small in size. The device significantly enhances the possibility of being able to accurately and quickly screen personnel, equipment, and materials at security checkpoints, military operations, law enforcement, or other screening scenarios, and for detecting trace explosive materials, night or day, very high humidity and bad-weather conditions. The system allows users to precisely and quickly detect different explosive chemical threat agents.

The system operates in a real-time fashion. It automatically and remotely collects samples and then dispenses a precise volume of chemical solutions over time when requested. The system optionally allows users to manually control the sequence of the pumping process. The system provides users with pump controls for dispensing chemical solutions. Through the built-in heater, the system automatically heats up the swiped sample to predetermined temperatures over specific time parameters using an automatic ramped heating feedback control. The system automatically and continually performs self-check and monitors fluid levels, temperature and time. The system automatically chronologically analyzes and stores data and arranges according to positive results versus negative results. The system automatically tells the operator to remove the analyzed swipe. The system delivers a unique sequence of precise chemical volumes under time, heat, and vapor parameters. The system has detachable and expendable chemical(s) in cartridge form for ease of replacement. The system uses a high-resolution digital camera for data collection and un-biased automated analysis.

By use of a wired or wireless transceiver, detected information can be easily transmitted to anywhere in the world. By replacing disposable swipes/pads/swabs and disposable chemical test reservoirs, the system can detect a wide range of explosives, clandestine material, drugs, and household products used to manufacture explosives, a range of controlled chemical agents, drugs, and narcotics etc. By allowing the user to swipe test materials and running computerized diagnostics, the user can easily and effectively change the system to meet what is considered to be the threat at that time. By having all components under program control and by arranging for a known input to the system such as a controlled injection of target material, the system can perform self-calibration and self-diagnostics.

By supporting third parties to review the scan data, the system enables police personnel to have access to experts in case of uncertainty. This access is convenient and enables third party access to full scan data as thought the experts are present at the point of police presence.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which.

DESCRIPTION

The following detailed description of the invention is provided to aid those skilled in the art in practicing the present invention. Even so, the following detailed description of the invention should not be construed to unduly limit the present invention, as modifications and variations in the embodiments herein discussed may be made by those of ordinary skill in the art without departing from the spirit or scope of the present inventive discovery.

Figure 1A:
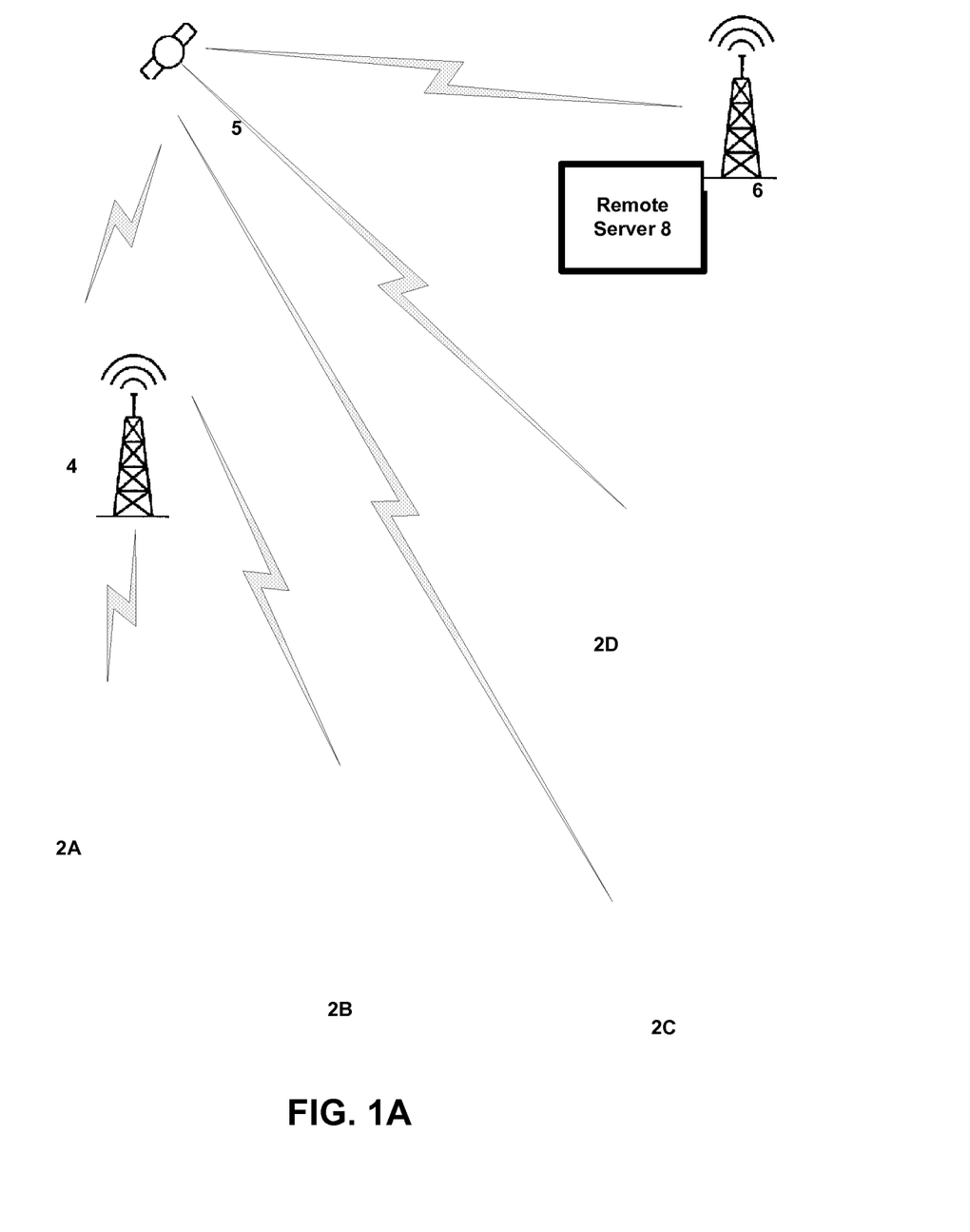
FIG. 1A shows a police cruiser system for detecting the presence of explosives and other controlled substances such as drugs or narcotics as well as other chemicals used in clandestine activities.

FIG. 1A shows a system for the detection of explosives and other controlled substances such as drugs or narcotics as well as other chemicals used in clandestine activities mounted in police vehicles 2A-2D. In FIG. 1A, each of police cruisers 2A-2D contains one or more detectors or testers such as those of FIG. 2. Within each of police cruisers 2A-2D, the detectors can communicate using a long range transceiver such as a cellular transceiver or to a satellite transceiver to a satellite 5, for example. The result of the transmission is received by a remote monitoring through a communication tower 8 center (not shown) and a remote server 8 and suspicious vehicles or people can be detained for additional query if needed.

The network delivers mission-critical information to officers' in-car laptops, providing such information as outstanding warrants and the location of other police vehicles in the area. The system enables greater information sharing and coordination between police officers on patrol, and as a result officers are more aware of their surroundings, more efficient at fighting crime, and safer on the job.

In one embodiment, the system operates with a 450-megahertz radio network to provide a mobile-to-base connection to a server, with a transmission speed of up to 4800 baud. The countywide wireless network provided officers in several jurisdictions with enough data bandwidth to run/re drug testing, license plates, check wanted listings, and send text messages.

The computer-aided dispatch system proved a more effective model for improving public safety, as it expanded the capabilities of the original wireless network to include global positioning system (GPS) mobile unit tracking, area maps, enhanced communication and more detailed case information on each mobile unit's onboard computer. Further, the dispatch system automatically stores records, case numbers, and other pertinent details regarding each call, which reduces the need for officers to fill out reports on minor incidents.

Using the 800-megahertz radio network, the system provides data transfer abilities to mobile units through Motorola data radio modems installed inside the vehicles. With a coverage area of about 30 square miles, the network allows officers to travel across the county and even into surrounding counties. Most of the files required by the computer-aided dispatch system reside on the in-car laptops, so only text or small data files are transferred via the 9600-baud narrowband 800-megahertz radio network.

In another embodiment, a wireless network with 802.11b hotspots around the city through wireless access points and integrated wireless cards is used to push Internet connectivity of up to 11 megabits per second to the in-car laptops. Each hotspot covers an area of about 150 feet indoors and up to a mile outdoors. With the mobile wireless solution, dispatchers send calls directly to the in-car laptop, ensuring that officers have accurate and complete information.

After responding to a call and testing for drugs using the drug tester, police officers use records management software to create reports in their cars and then transmit the reports to the office over the 802.11b or 800-megahertz network. This remote capability has nearly eliminated the need for officers to return to headquarters to fill out and file routine paperwork. Reports generated in the field are more accurate, as well, because the details are still fresh in the officers' minds. For some routine calls, such as alarm responses, details are recorded in the computer-aided dispatch system automatically, so officers do not need to fill out any paperwork.

Aside from the 800-megahertz and 802.11b wireless networks d, there are other options such as a WiMax municipal area network, also known as an 802.16 network, that provides high-throughput broadband connections over long distances. This type of network provides cost-efficient Internet access by converging all connections into a single Internet connection. Municipalities can deploy WiMax networks to push Internet connectivity to mobile units or IP-based equipment, such as video cameras, located within a defined area. A WiMax network can provide access in a linear service area of up to 30 miles at a data rate of up to 70 megabits per second. This type of network is based on a centralized, fixed Internet connection broadcasting a wireless signal to multiple locations within the area. Commonly, the base station antenna is located on a rooftop or other tall structure, such as a water tower. The broadcast signal is then routed to a single computer via Ethernet cable to an 802.11 hotspot wired Ethernet LAN.

Figure 1B:
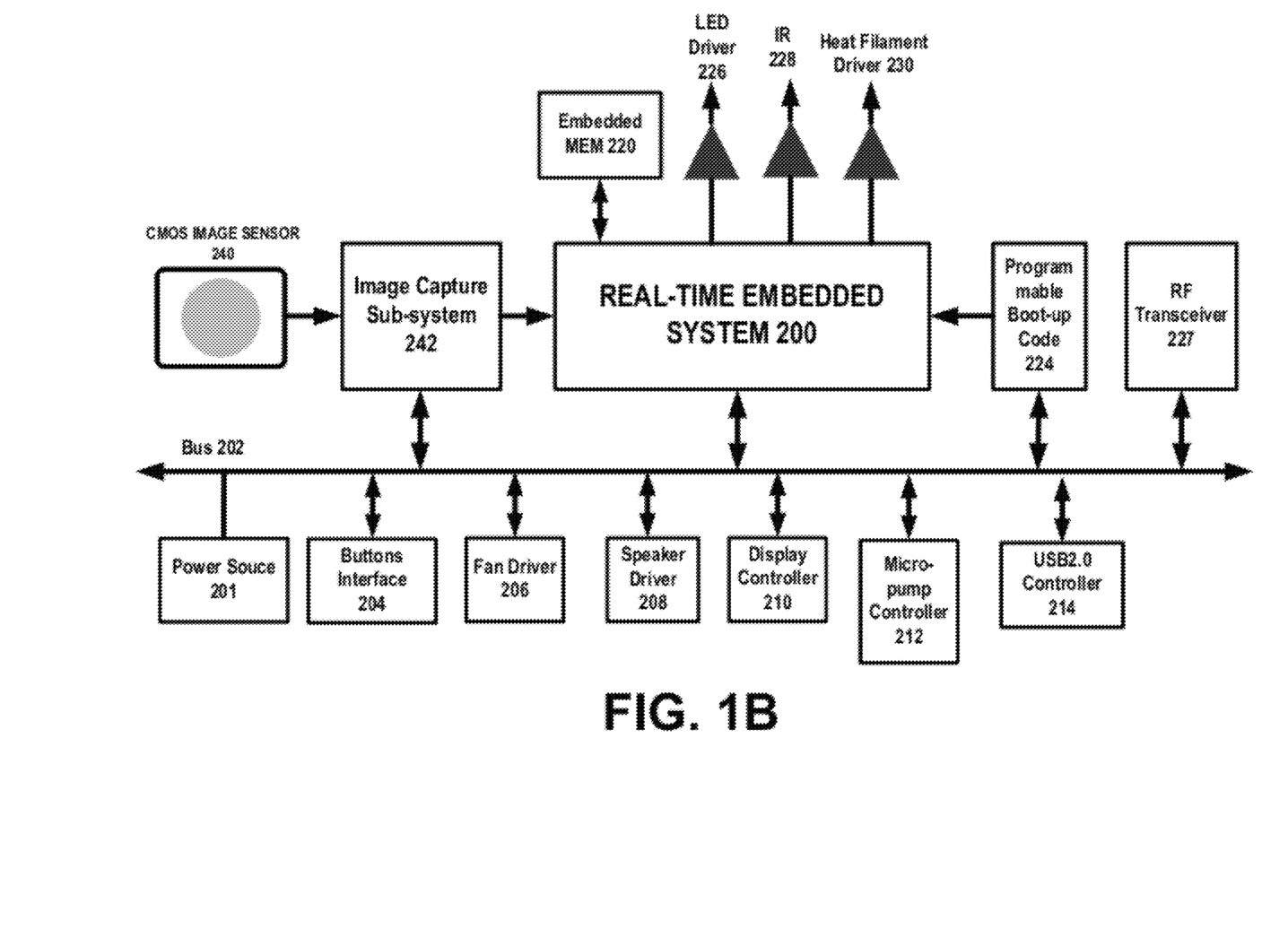
FIG. 1B shows an exemplary block diagram of processing electronics for detecting drugs or explosives.

FIG. 1B shows an exemplary block diagram of processing electronics for the tester used by police field personnel. A processor 200 controls all tasks done by the system. The processor 200 communicates over a bus 202 to various devices, including buttons interface 204, fan driver 206, speaker driver 208, display controller 210, micro-pump driver 212, and USB controller 214. The processor 200 also communicates with embedded memory 220 and a programmable ROM 224 that contains boot code as well as application code. The processor 200 also drives buffers 226, 228 and 230 which controls the LED(s), infrared sensor that informs the operator if a swipe has been loaded into the test chamber 38, and heat filament, respectively. The infrared sensor is positioned under the swipe and acts as a proximity sensor to detect the presence or absence of a swipe by the amount of light reflected back. The processor 200 or controller actuates the motor to drive a solution delivery manifold to the center of the swipe and in close proximity to the swipe to dispense the solution without dripping, regardless orientation. The controller can monitor fluid levels within each reservoir contained in the disposable cartridge. This is done by decrementing available volume each time the pump is actuated and when the count reaches a low threshold, the controller can indicate that the reservoir is out of chemical.

A rechargeable power source 201 such as a battery can be used to power the camera and processor. The power source 201 can be charged by a vibrational energy scavenging charger such as the Volture Vibration energy harvester from Mide Technology Corp of Medford, Mass., for example. The Volture is a robust, reliable and inexpensive means to harvest vibration energy for the detector. The Volture vibration energy harvester device harvests otherwise wasted energy from mechanical vibrations of the carrier such as the train or ship vibrations. Piezoelectric materials convert mechanical strain into useable electrical energy. The piezoelectric materials are enclosed in a protective skin with pre-attached electrical leads, producing a highly reliable component with no soldered wires. The QuickPack actuator's protective skin also provides electrical insulation and defense against humidity and harsh contaminants.

The system can operate without rechargeability as well. The system is powered by a power source 201 such as a 12-volt DC source, which can be generated from an AC/DC converter, a car outlet or from eight 1.5-volt batteries in series. In one embodiment that does not use rechargeable power source, the highest prioritized energy source is from an AC/DC converter followed by the one from a container power outlet, then the energy from batteries. The 12-volt DC power source will supply current to the heater and the pump. It is also connected to the low drop voltage regulator to generate different voltage levels such as 5 V, 2.8 V and 3.3 V, which are necessary for the processor and for other peripherals as well.

The system has a radio-frequency transmitter/receiver (transceiver) 227 which can communicate with the local computer 1, or can send data through mesh networking by transmitting the data from container to container node until the data reaches its destination. The destination can be another container 2A, 2B, 2C, or 2D, or can be the local computer 1 for long range transmission to the local server 8.

In one embodiment, the transceiver 227 uses the WiFi (802.11) protocols. In another embodiment, the transceiver uses the ZigBee (802.15) protocols. The protocols automatically construct a low-speed ad-hoc network of nodes. In most large network instances, the network will be a cluster of clusters. It can also form a mesh or a single cluster. The current profiles derived from the ZigBee protocols support beacon and non-beacon enabled networks. In non-beacon-enabled networks (those whose beacon order is 15), an unslotted CSMA/CA channel access mechanism is used. In this type of network, ZigBee Routers typically have their receivers continuously active, requiring a more robust power supply. However, this allows for heterogeneous networks in which some devices receive continuously, while others only transmit when an external stimulus is detected. In the heterogeneous network, the ZigBee node that is connected to the mains supply is constantly on, while a battery-powered transponder would remain asleep until it is periodically wakened up to test for the presence of a target chemical. The transponder then sends a command to the mains powered transponder, receives an acknowledgment, and returns to sleep. In such a network the mains powered node will be a ZigBee Router, if not the ZigBee Coordinator; the battery powered node is a ZigBee End Device. In beacon-enabled networks, the special network nodes called ZigBee Routers transmit periodic beacons to confirm their presence to other network nodes. Nodes may sleep between beacons, thus lowering their duty cycle and extending their battery life.

In general, the ZigBee protocols minimize the time the radio is on so as to reduce power use. In beaconing networks, nodes only need to be active while a beacon is being transmitted. In non-beacon-enabled networks, power consumption is decidedly asymmetrical: some devices are always active, while others spend most of their time sleeping. The basic channel access mode is "carrier sense, multiple access/collision avoidance" (CSMA/CA). That is, the nodes talk in the same way that people converse; they briefly check to see that no one is talking before they start. There are three notable exceptions to the use of CSMA. Beacons are sent on a fixed timing schedule, and do not use CSMA. Message acknowledgments also do not use CSMA. Finally, devices in Beacon Oriented networks that have low latency real-time requirements may also use Guaranteed Time Slots (GTS), which by definition do not use CSMA.

The system of FIG. 1B can detect the presence of a predetermined substance by applying a sequence of chemicals onto the test swipe pad and taking an image of the result and performing image processing to detect changes on the test swipe pad. One example of the of a sequence involving chemistry time, temperature ramp rates and hold times to optimize each of the results for explosives, drugs, or other threat chemicals within a chemical reaction sequence. The system always adjusts the start temperature prior to running a particular sequence to a predetermined temperature value. An example of the temperature may be 35° C. where the swipe retaining a wet or dry sample is adequately held and in intimate contact with the elements of the swipe holder. The specific parameter controls for fan speed, LED lighting, pumping increments, GUI, camera, speaker, or display can be varied, as known to one skilled in the art.

The background image of the swipe at this temperature is taken so as to subtract out any colors that may be present on the swipe prior to analysis. A selected chemical reactant from one of the reservoirs is then pumped onto the swipe in a non-drip fashion and in a volume of 20-30 μL, most favorable being 25 μL. The system takes second image of the chemically reacted sample on the swipe and immediately processes this image from subtracted background for color indicating peroxides. The second image then becomes the new background image whether peroxides are present or not for the next analyte sought hexamethylene triperoxide diamine HMTD.

Further reacting sample material on the swipe, the heater element begins rapidly heating only the sample area on the swipe with temperature setting ramp rates of 10-20° C. per minute to 115° C., most favorable being 15° C. per minute. During the ramp, a third image is taken between 5-15 seconds, 12 seconds being most favorable, to analyze for color indicating HMTD. The system takes third image of the chemically reacted sample on the swipe and immediately processes this image from second background for presence of HMTD. Once the heater element reaches 115° C., it then holds a for 20-40 seconds, 30 seconds being most favorable. The third image then becomes the new background image whether HMTD was present or not for the next analyte sought triacetone triperoxide TATP.

During the hold time, a fourth image is taken of the chemically reacted sample on the swipe at 25 to 30 seconds, 28 seconds being most favorable, and immediately processes this image from third background for presence of the color indicating TATP. The fourth image then becomes the new background image whether TATP was present or not for the next analyte sought chlorates.

During the same hold time, a fifth image is taken of the chemically reacted sample on the swipe at 25 to 35 seconds, 30 seconds being most favorable, and immediately processes this image from fourth background for presence of the color indicating chlorates. The fifth image then becomes the new background image whether chlorates were present or not for the next analyte sought TNT.

The heater element begins rapidly heating only the sample area on the swipe with temperature setting ramp rates of 10-20° C. per minute to 140° C., most favorable being 15° C. per minute. Simultaneously, a second selected chemical reactant from one of the reservoirs is then pumped onto the swipe in a non-drip fashion and in a volume of 20-30 μL, most favorable being 25 μL. Once the heater element reaches 140° C., it then holds for 10-20 seconds, 10 seconds being most favorable. During the second temperature ramp, a sixth image is taken between 5-15 seconds, 8 seconds being most favorable, to analyze for color indicating TNT. The sixth image then becomes the new background image whether TNT was present or not for the next analytes sought all high explosives.

The heater element begins rapidly heating only the sample area on the swipe with temperature setting ramp rates of 10-20° C. per minute to 155° C., most favorable being 15° C. per minute. Simultaneously, a third selected chemical reactant from one of the reservoirs is then pumped onto the swipe in a non-drip fashion and in a volume of 20-30 μL, most favorable being 25 μL. Once the heater element reaches 155° C., it then holds for 10-20 seconds, 20 seconds being most favorable. During the third temperature ramp, a seventh image is taken between 5-15 seconds, 5 seconds being most favorable, to analyze for colors indicating all high explosives. The seventh image then becomes the new background image whether high explosives were present or not for the next analytes sought all nitrates.

The heater element continues to hold at 155° C. and from 10-20 seconds, an eighth image is taken between 10-20 seconds, 15 seconds being most favorable, to analyze for colors indicating all nitrates. The heater element immediately cools down for the next sample run.

Another example of a single test involving chemistry time, and temperature settings and hold times to optimize results for a chemical reaction involves depositing one or more of the chemical reactants from their respective reservoirs onto the swipe in a non-drip fashion. This is to impart a single spot test or multiple spot tests for a single drug or drugs, a single explosive or explosives, or other threat chemicals at ambient or preset temperature conditions that results in a single color or an array of colors unique to that material under the temperature settings and reagents applied.

The detection system of FIG. 1B significantly enhances the detection of the explosive materials. First, the device is preprogrammed and/or is remotely controlled to automatically rotate a swipes within the holder for intermittent and/or long term particle and/or vapor sampling by rotating a single swipe filter into position with connection to a pump or fan. A blank swipe filter on the opposite side of the holder may optionally be analyzed at the same time to provide a background level.

Pumps or the automatically pumps a series of chemical solution agents into the swiped sample and heats up to specific temperature to accelerate the chemical reactions. Second, an internal CMOS camera captures the chemical reaction images at its highest resolution, raw data for better image analysis. Third it then sends these raw images data to the LCD (Liquid Crystal Display) screen for the purpose of observation. Moreover, the JPEG codec is capable storing and replaying image functions. The LCD screen provides a high quality image for human viewing. In another embodiment, in place of JPEG, a bitmap image or an MPEG video or any suitable imaging storage format can be used. The LCD can analyze the image to identify explosive materials based on the provided chemical reaction database. Last but not least, the PC interfaces can be used to update software and firmware as well as to backup the data.

In one implementation, to start the analysis process, the system turns the micro-pump(s) N (i.e., N=1, 2, 3 . . . or a combination thereof) to disperse the chemical solution into the Swiped Sample. The pumping rate is set to 2 Hz. After dispersing chemical solution, the system starts heating the sample to excite the chemical reactions under controlled vapor, time, temperature, and chemical volume conditions specific to a particular analyte or group of analytes. A current of about one ampere is applied to heat up the heating filament. During the heating process, the fluctuation of the temperature is controlled by a feedback circuit with a thermistor.

When the temperature of the sample swipe reaches a predefined value, the system turns the heater off, the white light LED on and the fan on. The speed of the fan is adjustable using pulse width modulation control in one embodiment.

Before commanding the camera's CMOS image sensor to capture an image, the system waits for the chemical reaction to complete for around 1 ms. The captured image is then displayed on the LCD.

The system creates a result image by subtracting the captured image from the background one. Then the result image is compared with the color patterns in the lookup table stored in the system. If the results image matches some color pattern, the result probability will be displayed and an optional audible alarm is given or not. Otherwise, an appropriate message is displayed on the LCD.

During the process of writing to the memory, (e.g., saving results or updating database), the system is able to detect the memory capacity and give the user a warning of full memory. In such a case, the user needs to clear the memory by deleting certain files before commanding the system to continue its work.

In one embodiment, the system executes a prime pump procedure to clear up air and chemical bubbles in the tubes of minimized length and diameter once the system has been idled for more than two weeks. If the system has not been used for the past two weeks then the system automatically rotates a swipe into position for automated priming of the pumps. During the prime pumps, the camera captures the image from the swipe and displays it on the LCD screen. During the prime pumps, no heat is applied to the swipe.

In one embodiment, in the main menu, before the unit is placed in the container, the user can see the date, the time and current status of the system. The system can generate a warning alarm once battery, chemical level and memory reach their minimal levels. The menu also contains three (3) software programmable buttons, namely New Analysis, Previous Results, and Settings. User can interact with these soft buttons by using the five hard buttons. The New Analysis option is highlighted as default. The usage of these soft buttons is as follows:

New Analysis: allows user to perform a new test.
Previous Results: allows user to trace back the data tested in the past.
Settings: allows user to set parameters such as date, time, to test the system reliability, or to connect to PC for firmware and/or database update.

The user can see the images taken by the camera. The system status is also displayed. In addition, three (3) soft buttons (Start, Stop, and Status) are provided for manual inspection if needed.

Each container tester can work with a user replaceable chemically treated pad, or can work with a swipe cartridge that is automatically advanced by a motor upon request. In a user replaceable pad arrangement, the container can only be tested once and the pad must be replaced before another test can be done. For example, if the container is opened at a port, before a ship goes through inspection, the container area is sealed off and an agent can go through each container and replace the pad at each point where third parties may have had access to the container and retest each container. For containers that need frequent testing, a motorized roll of chemically treated pad is provided and upon actuation, the roll can be advanced to expose the next chemically treated pad for testing.

In one embodiment, the chemically treated pad has a substantially round shape. A sequence of one or more chemicals can be delivered to the pad to detect an explosive compound. Each chemical or chemical sequence in tandem with temperature parameters over time causes the pad to display a color unique to the explosive compound. The sequence of chemicals are deposited onto the pad at predetermined times. The sequence of chemicals is deposited onto the pad at predetermined temperature range(s) achieved at a specific ramp rate. The sequence of chemicals is deposited onto the pad at predetermined hold time(s) each at predetermined temperature range(s). Each chemical deposited under predetermined time and temperature conditions reacts to a specific explosive or class of explosives to yield a specific color unique to that explosive. The chemically treated pad can be a substantially round shape of thickness less than 0.005 inches to achieve rapid, and even heating through the material layer, and adapted to receive a sequence of one or more chemicals to detect an explosive compounds. The base can have a non reflective dull black color. The pad region can be a cloth within a white zone on the base and an ink free border. The round swipe can be used for explosives in which a sequence of unique chemicals are deposited onto the same circular pad at specified times, temperature ramp rates, and hold times at a given temperature. Each chemical deposited under these time/temp conditions will react a specific explosive or class of explosives yielding a specific color unique to that explosive or class of explosives.

In another embodiment, a chemically treated pad can be a substantially four-sided shape with a plurality of test regions. A plurality of unique chemical solutions can be deposited on each test region. The chemical solutions can be deposited separately or at same time to the respective test regions on the swipe. One or more chemicals can be deposited onto the pad to detect one or more drug compounds. Each chemical causes the pad to display a color unique to the-drug compound. The colors generated on each pad, in combination, subsequently generate a color bar code unique to the drug or class of drugs. The sequence of chemicals are deposited onto the pad at predetermined times. The sequence of chemicals are deposited onto the pad at predetermined temperature range(s). The sequence of chemicals are deposited onto the pad at predetermined hold time(s) each at predetermined temperature range(s). Each chemical deposited under predetermined time and temperature conditions reacts to a specific explosive or class of explosives, drug or class of drugs to yield a specific color unique to that explosive or drug. The chemically treated pad can be a substantially four-sided shape of thickness less than 0.005 inches to achieve rapid and even heating through the material layer, and adapted to receive a sequence of one or more chemicals to detect a drug compound. Four different solutions can be deposited at same time to the respective rectangles on the swipe. The portable test device (FIG. 1B) will read the "color bar code" results to determine certain drugs. Then, the swipe will be heated through one to several heat ramp cycles to invoke more color changes to each of the respective rectangles creating new color bar codes. Each color bar code at a specific temperature and time will indicate a specific drug or clandestine material sought. A sampler/applicator can be used to sample a suspect material; in a baggie for example; and wipes the collected drug sample onto the square swipe pad.

The swipe pad may be formed of material that may be resistant to chemical degradation during testing in the approximate pH range of 0.1 through 14 to avoid reacting or decomposing. The swipe pad may be white in color to aid test evaluation, may be heat resistant and chemically resistant at elevated temperatures up to approximately 150° C. and may have hydrophilic properties for wetting only when using fluid reagents in the test apparatus. The swipe pad may also be roughened, for example, by use of a woven material, to aid in retrieving test sample particles from the environment. The swipe pad may also be thick enough to resist damage such as tearing during sampling, yet not be too thick such that heating of the test sample is inhibited. A thickness less than 0.005 inches to achieve rapid, and even heating through the material layer.

The test swipe can be used to swipe a sample to identify a chemical composition. This can be done by clamping the test swipe under a camera and above a heater, the test swipe having a base; a chemically treated pad containing the swiped sample positioned above the base in a white zone; and a tab attached to one side of the base; automatically pumping a series of chemical solution agents into the swiped sample without dripping so that the device may be held in any orientation; heating the swiped sample to one or more accurate predetermined temperatures and hold times to optimize and accelerate the chemical reactions; evacuation of vapors generated, capturing one or more images of the chemical reaction; sending the images to the a display screen for operator observation; and analyzing the images to identify the chemical composition based on a chemical reaction and sequence of occurrence and database.

The chemical solution agents are described next. A Tetrabutylammonium hydroxide formulation may be used in a reagent test to impart a color to nitroaromatic compounds that may otherwise not be detected by other bases, such as, sodium hydroxide or potassium hydroxide regardless of their respective concentrations. The tetrabutylammonium hydroxide may also be strong enough to create nitrite salts for other types of explosives that may be in the test sample in preparation for testing with a second type reagent. Use of tetrabutylammonium hydroxide may be difficult due to limited shelf life and its reaction to environmental carbon dioxide that may degrade the necessary color chemistry with nitroaromatics. To develop a solvent system mixable with water to inhibit degradation and reduce hazardous effects to a user, an ethanol and water mixture may be used to inhibit tetrabutylammonium hydroxide degradation with the ethanol ratio such as not to be flammable. The ethanol and water may also have minimum nitrite content to avoid reaction to a second type reagent test that may give false positive results. The tetrabutylammonium hydroxide may also be of a concentration in the ethanol water mixture so as not to interfere chemically with subsequent formulations added to the swipe. For example, if a 10 nanogram detection threshold may be used, any nitrite content in the solutions may be less than 0.2 nanograms per microliter of fluid to minimize corruption of test results or false detection.

The first reagent test may use a first reagent fluid that may have an optimum detection performance range with the fluid having a tetrabutylammonium hydroxide in a water solution in the approximate range of 65-850 percent and an ethanol as approximately 20-35 percent of the water solution. Test results may be obtained using a wider tolerance of elements in the first reagent fluid, but there may be reduced detection sensitively. The tetrabutylammonium hydroxide in water solution may be in the approximate range of 0.1 to 1.6 Molar and the ethanol as approximately 5 to 95 percent of the water solution. Also, other alcohols or blends of alcohols may be used in place of ethanol; however, for example, methanol may be toxic to the user and isopropyl may be less toxic, but may have poorer detection sensitivity results and cause shorter shelf life for the reagent fluid.

A second reagent test may be a Griess reagent test. The Griess reagent may cause a highly colored azo dye to be created in a reaction with nitrite salts generated from the first reaction or present as residue from firearms. The acid that may be used in the formulation of the second reagent may be phosphoric acid that reduces hazardous effects to a user that may become a buffer during the reaction thereby buffering against itself to inhibit creation of too much acid on the swipe pad. Other types of acids that may be used in the Griess test may react too violently with other bases, may be toxic or hazardous, or may create a strong odor.

The phosphoric acid may be mixed with sulfanilic acid and N-(1-naphthyl) ethylenediamine dihydrochloride. The sulfanilic acid may be water soluble with reduced toxicity in combination with and it may impart a deep magenta or fuchsia color to the test sample for ease of detection of explosives. N-(1-naphthyl) ethylenediamine dihydrochloride may be water soluble and not carcinogenic as with other salts, and may impart an effective color reaction from the test sample. The second reagent solution may use deionized water that may have minimum nitrite content to reduce false positive test results. For example, if a 10 nanogram detection threshold may be used any nitrite content in the solutions may be less than 0.2 nanograms per microliter of fluid to minimize corruption of test results or false detection.

The second reagent test may use a second reagent fluid that may have an optimum detection performance range with the fluid having a phosphoric acid in a water solution in the approximate range of 1.3 to 1.7 Molar; and a sulfanilic acid of approximately 8 grams with a N-(1-naphthyl) ethylenediamine dihydrochloride of approximately 5 grams per 1000 milliliters of the phosphoric acid in water solution. Test results may be obtained using a wider tolerance of elements in the second reagent fluid, but there may be reduced detection sensitivity. The phosphoric acid in water solution may be in the approximate range of 0.1 to 7.35 Molar, the sulfanilic acid may be in the approximate range of 5 to 8 grams, and the N-(1-naphthyl) ethylenediamine dihydrochloride may be in the approximate range of 5 to 9 grams. Other acids, acid combinations, or acid concentrations may be used, but may produce less than optimal testing sensitivity results. Other solutions may have increased acidity and be hazardous to the user as well as have a detrimental effect on the testing device.

Other solutions may not be acidic enough for a detection reaction to occur or may be toxic. Other salts may be used, but they may reduce the explosives detection sensitivity.

Figure 1C:
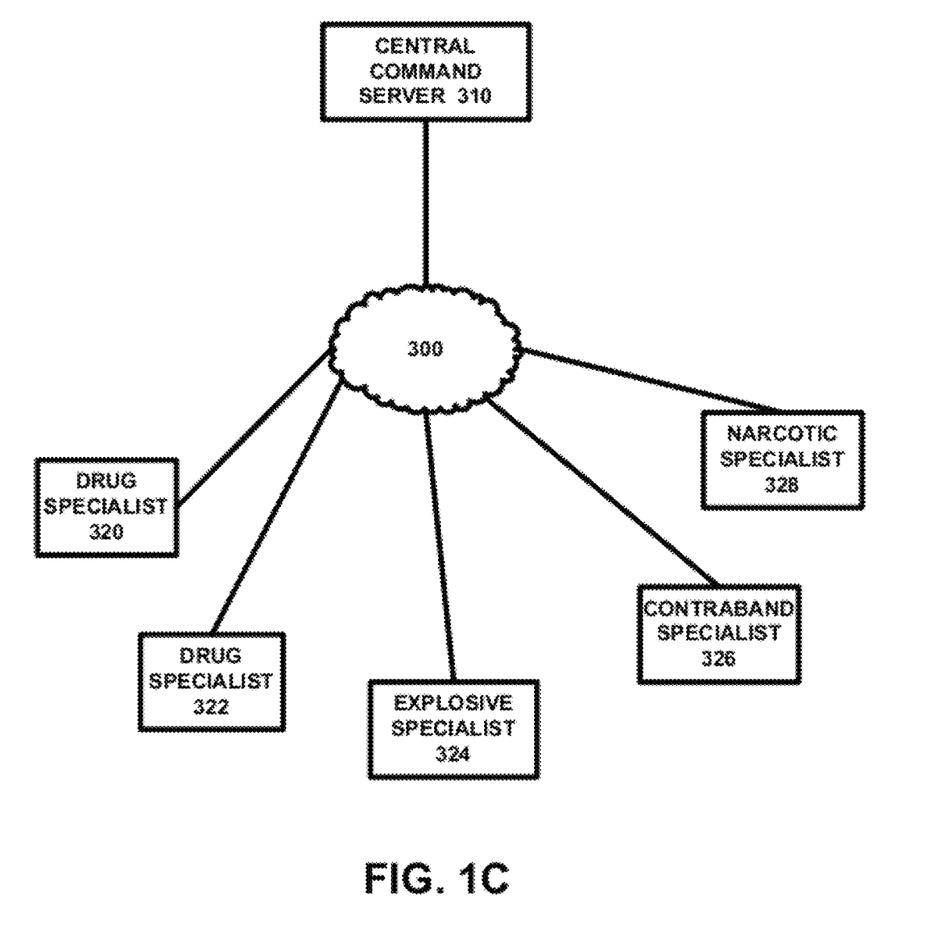
FIG. 1C shows an exemplary network to assist police personnel with identifying a particular substance.

FIG. 1C shows an exemplary network to assist police personnel with identifying a particular substance. The system of FIG. 1C includes a central command server 310 run by a police department. The server 310 receives information collected by officers and sent to the remote server 8 (FIG. 1A). The server 310 then accesses a wide area network 300 such as the internet. The server 310 communicates with a plurality of specialist workstations 320-328 and upon proper authentication, sends the swipe scan data to the specialists for additional analysis and consultation with police field personnel or police headquarter's if needed.

Figure 2:
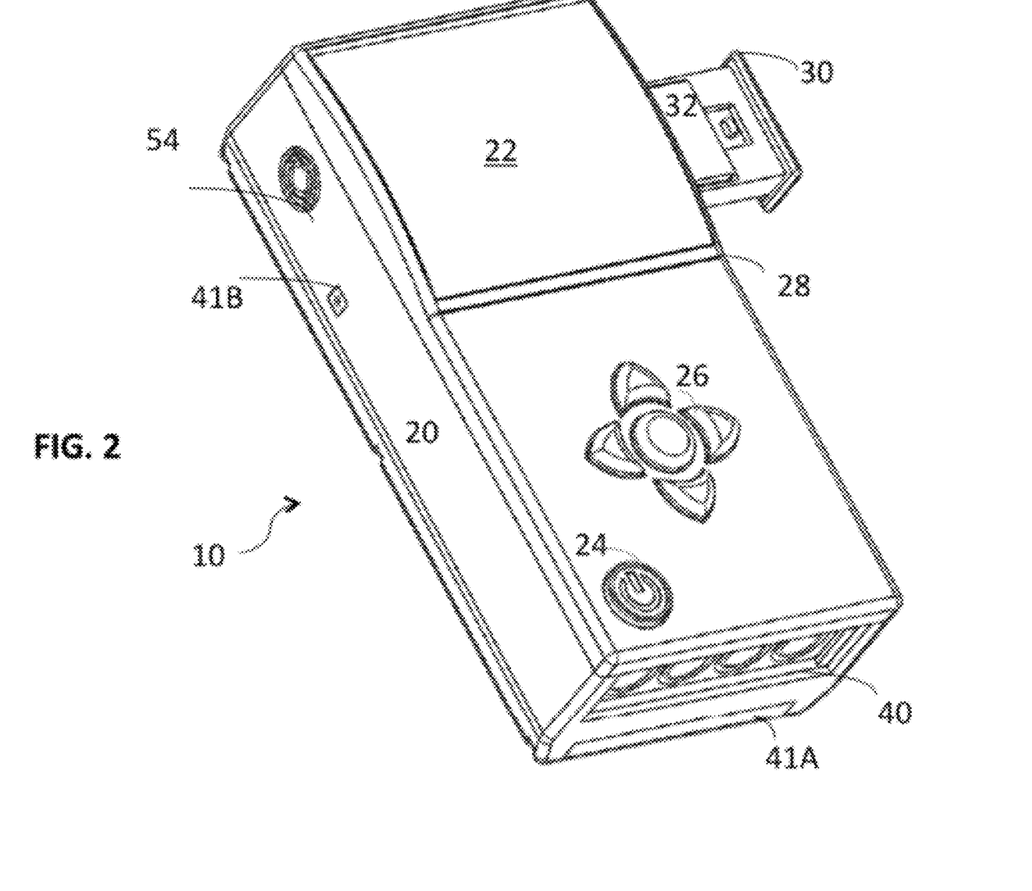
FIG. 2 shows an exemplary portable chemical detection device.

FIG. 2 shows an exemplary portable chemical detection device 10 that uses the test swipes discussed above. The device 10 can be secured to the exterior of the shipping container, or can be placed inside the shipping container and suitably connected to an antenna that allows wireless communication to take place with the device 10. The device 10 has a housing 20 that supports an optional display 22 and input devices such as an on-off button 24 and navigation/selection buttons 26. In one embodiment, the system has six buttons. The first button is the On/Off button. This button allows user to turn the unit on or off. The remaining five buttons (Left, Right, Down, Up, and Enter) allows a user to interact with a Graphical User Interface (GUI) of the system. The GUI is flexible, efficient and user friendly.

The device 10 also has an input/output port 28 such as a USB port or Firewire port to communicate with a remote computer, and AC power port, among others. In one embodiment, the I/O port 28 is a weather proof PC interface. The PC interface can set up operation parameters and recover analyzed data. In another embodiment, the I/O port 28 can include a flash memory card interface.

The device 10 also includes two ports 30 and 40 to receive user replaceable media and chemical. The device 10 also includes a port 41A to receive user replaceable DC battery cartridge. Port 30 receives a test swipe that is manually inserted by an operator in the embodiment of FIG. 2, although the present inventors contemplate that test swipes can be roll-mounted and moved to position through a motorized mount, for example. The port 40 receives a chemical cartridge, which can house one or more chemical containers. An electronic controller receives inputs from the buttons or keys and controls the display 22 and other electronics in the device 10. The system can work with different power sources including battery port 41A port and/or a DC input port 41B such as a 12V jack or an AC/DC adaptor.

To test a contaminate collection swipe, a user opens the port 30 and places a test swipe into a swipe holder. The swipe holder moves along sliding rails when the user closes the port 30 to place the test swipe under a test chamber. The test chamber includes a chamber with two openings that face a variable speed fan 54 to draw air across the test swab or test swipe while under test. The test chamber also includes a heating element 56 (not shown) connected to a PID loop that can warm up the test swab to multiple predetermined temperature settings during test. The test chamber also contains a camera 39 (FIG. 4).

Figure 3:
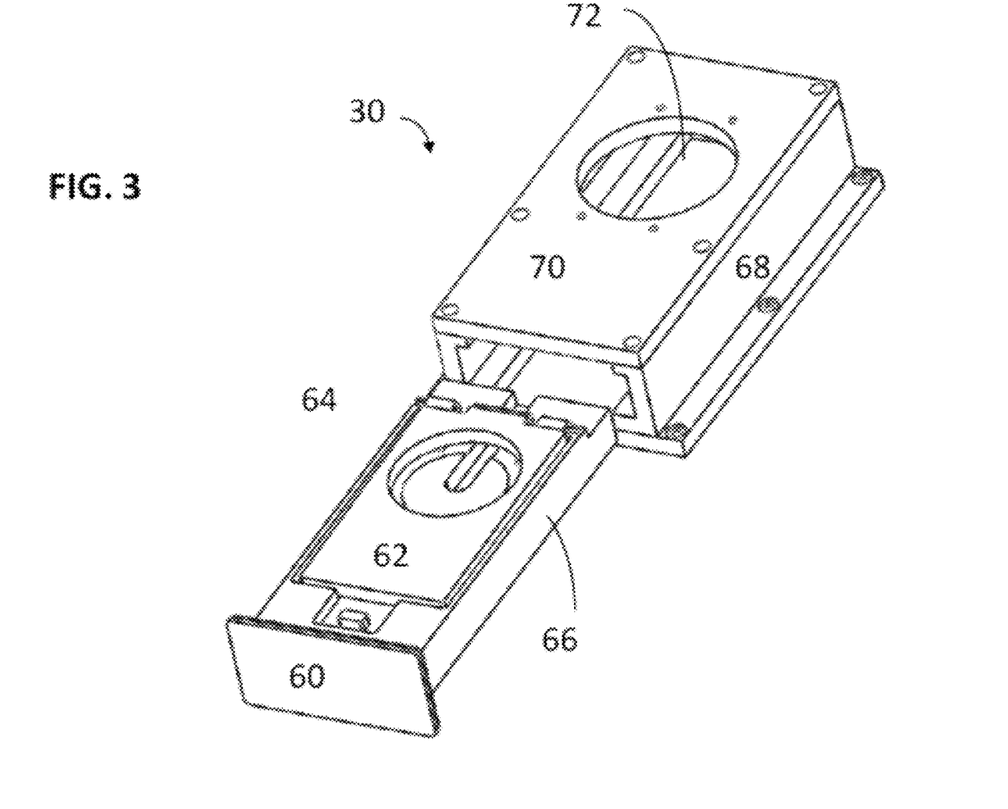
FIG. 3 shows in more details a swipe receiving port.

FIG. 3 shows in more detail port 30 that receives the test swipe in the swipe holder 64. The swipe holder 64 includes a door 60 by which a user can press against to open or close the port 30. The swipe holder 64 also includes an open face press-fit clamp 62 that secures the swipe against a heating element under the swipe upon closure. The swipe holder 64 is attached to rails 66 that slide within rails 68 to enable the swipe holder 64 carrying the test swab to move in and out of the device 10. An enclosure for the swipe holder 64 is formed by positioning a lid 70 with an opening 72 between the sliding rails 68. The opening 72 allows movable tubes from the micro-pumps (not shown) to dispense test chemicals onto the swipe. The opening 72 also allows a camera 39 (FIG. 4) to capture images of the test results for automatic real-time analysis of the test. A white-light source such as one or more LEDs are positioned near the camera can be turned on to provide lighting if needed and turned off when not used to conserve power. In one embodiment, the camera output is shown on the display 22 (FIG. 2) so that the user or operator can visually determine the test result(s) while the automated determination is in progress. The opening 72 also allows a variable speed fan 54 (FIG. 4) to gently move vapor away from the camera lens to avoid fogging the lens (anti-fogging).

Figure 4:
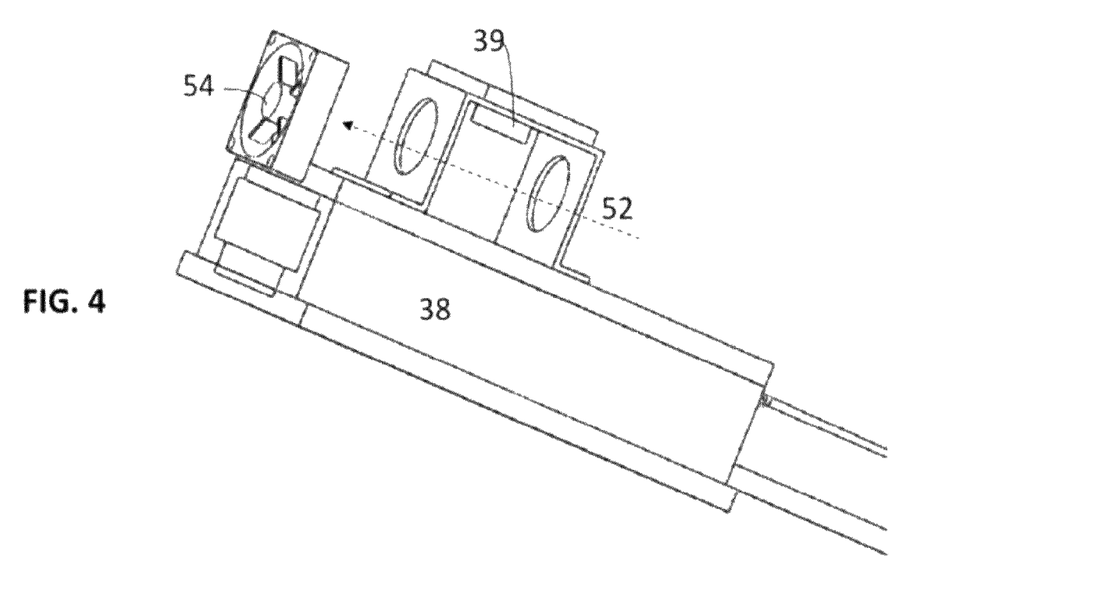
FIG. 4 shows an exemplary perspective view of a camera in a test chamber.

FIG. 4 shows an exemplary perspective view of a camera 39 in conjunction with the test chamber 38. The chamber 38 includes a motor driving a gear cooperating with a moveable arm that moves test tubing fixture back and forth over the test swab or swipe during testing. The test tubing fixture moves very closely to the swipe for chemical deposit onto the swipe when the device 10 is held in any orientation. The arm includes a plurality of piezoelectric pumps (not shown). The moveable arm also moves the fixture out of the way for the camera 39 to capture changes on the test swipe during testing. The camera images are then analyzed, and the result can then be displayed on the display 22 (FIG. 2). In one embodiment, the camera 39 can capture raw images with 65,536 colors. The camera is protected with an anti-fog feature using the adjustable speed fan 54. The image data can be shown continuously throughout the entire process on a flip-up display 22 with high fidelity. In one embodiment, the system provides a software JPEG (or alternatively bitmap) encoder and decoder for storing and viewing previous results and images. The system also includes white light LEDs (not shown) located within the test chamber 38 that provides even, shadow free, and uniform lighting during camera 39's operation with a programmable white light intensity. The LEDs minimize shadows in the camera viewing area.

The swipe holder 34 (FIG. 3) moves along rugged sliding rails 66 when the user closes the port 30 to place the test swipe under the test chamber 38 (FIG. 4). The test chamber 38 includes a chamber with two openings 52 that face the fan 54 to draw air across the test swipe while under test. The test chamber also includes a heating element (not shown) that can warm up the test swipe to a predetermined temperature during test.

Figure 5:
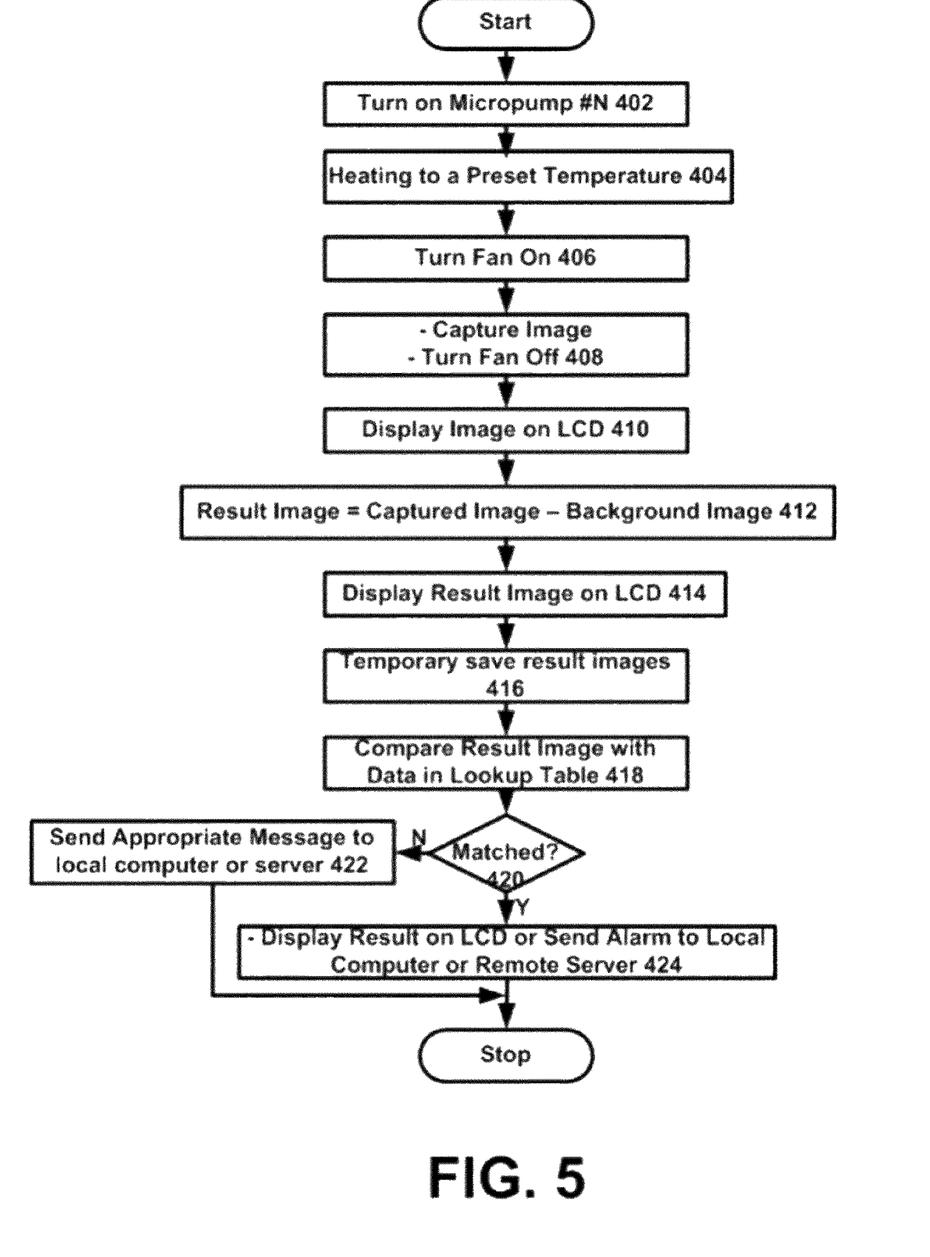
FIG. 5 shows an exemplary image analysis process executed by the system of FIG. 1B to test for the presence of a predetermined substance.

FIG. 5 shows an exemplary image analysis process executed by the real-time embedded system processor 200 to detect chemical agents automatically. To start the analysis process, the system turns the micro-pump(s) N (i.e., N=1, 2, 3 . . . or a combination thereof) to disperse the chemical solution into the swiped sample. The pumping rate is set to 0.250 Hz. After dispersing chemical solution, the system starts heating the sample to excite the chemical reactions. A current of about 1 Ampere is required to heat up the heater filament. When the temperature of the sample reaches a predefined value, the system turns the heater off, the LED and the fan on. In one embodiment, before commanding the CMOS image sensor to capture an image, the system waits for the chemical reaction to be optimized: time, temperature, volume dispensed, and vapor to complete for around 1 millisec. The captured image is then displayed on the LCD. The system creates a result image by subtracting the captured image from the background one. Then the result image is compared with the color patterns in the lookup table stored in the memory. If the results image matches some pattern, the result will be displayed and an alarm can be sent to the local computer 1 or the remote server 8, for example. Otherwise, if no dangerous substance has been detected, an appropriate message is sent to the computer or optionally displayed on the LCD.

In one embodiment, the system can remotely and automatically collect sample particles by air filtration on a series of swipes at under remote control or any pre-set, predetermined time. The system can analyze any or all swipes on command to identify a chemical composition collected according to date and time. In one embodiment, the system includes a series of pre-loaded swipes in a cartridge whereby the test swipes are clamped in the holder, rotated in and out of a air filtration position for any period of time controlled by the operator, and the test swipes may then be rotated under a camera and above a heater. The test swipe can have a base; a chemically treated pad containing the swiped sample positioned above the base; and a tab attached to one side of the base. The system can actuate a piezoelectric transducer or pumps that deposits a series of chemical solution agents into the swiped sample without dripping so that the device may be held at any angle of position or orientation; heating the swiped sample to one or more predetermined temperatures at a controlled rate and hold times to optimize and accelerate the chemical reactions. The system then captures one or more images of the chemical reaction; sends the images to the display screen for operator observation; and analyzes the images to identify the chemical composition based on a chemical reaction and sequence of occurrence and database.

Due to the automated, reproducible analysis, the system provides an objective indication of potential threats with more accurate, un-biased results at night, high humidity, or bad weather conditions, and therefore, more convenient.

The invention may be implemented in hardware, firmware or software, or a combination of the three. Preferably the invention is implemented in a computer program executed on a programmable computer having a processor, a data storage system, volatile and non-volatile memory and/or storage elements, at least one input device and at least one output device.

By way of example, a block diagram of a computer to support the system is discussed next. The computer preferably includes a processor, random access memory (RAM), a program memory (preferably a writable read-only memory (ROM) such as a flash ROM) and an input/output (I/O) controller coupled by a CPU bus. The computer may optionally include a hard drive controller which is coupled to a hard disk and CPU bus. Hard disk may be used for storing application programs, such as the present invention, and data. Alternatively, application programs may be stored in RAM or ROM. I/O controller is coupled by means of an I/O bus to an I/O interface. I/O interface receives and transmits data in analog or digital form over communication links such as a serial link, local area network, wireless link, and parallel link. Optionally, a display, a keyboard and a pointing device (mouse) may also be connected to I/O bus. Alternatively, separate connections (separate buses) may be used for I/O interface, display, keyboard and pointing device. Programmable processing system may be preprogrammed or it may be programmed (and reprogrammed) by downloading a program from another source (e.g., a floppy disk, CD-ROM, or another computer).

Each computer program is tangibly stored in a machine-readable, removable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

The invention has been described herein in considerable detail in order to comply with the patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What is claimed is:

1. A police tester to detect the presence of a target substance, comprising:
   a housing;
   a chemical reservoir insertable into the housing;
   a test swipe adapted to receive a chemical from the chemical reservoir, the test swipe including one or more chemically treated pads which, upon contact with one or more chemicals in concert with one or more heating and time profiles, displays a sequence of a plurality of color reactions unique to multiple analytes, including explosives, drugs, or household chemicals;
   a camera to capture an image from the test swipe;
   a processor coupled to the camera to process the image to detect the target substance;
   one or more dispensers coupled to the chemical reservoirs and controlled by the processor to dispense the chemical on the test swipe; and
   a heater coupled to the processor to ramp test swipe temperature according to the one or more heating and time profiles.

2. The tester of claim 1, wherein the chemically treated pad comprises a substantially round shape or rectangular shape.

3. The tester of claim 1, comprising a sequence of one or more chemicals delivered to the pad to detect an explosive compound.

4. The tester of claim 3, wherein each chemical causes the pad to display a color unique to the explosive compound.

5. The tester of claim 3, wherein the sequence of chemicals are deposited onto the pad at predetermined times or predetermined temperature range(s).

6. The tester of claim 3, wherein the sequence of chemicals are deposited onto the pad at predetermined hold time(s) each at predetermined temperature range(s).

7. The tester of claim 1, comprising a heater guard positioned between the test swipe and an electrical heater.

8. The tester of claim 1, wherein the remote computer comprises a server.

9. The tester of claim 8, wherein the server forward data captured from the test swipe to police personnel and one or more specialists.

10. The tester of claim 8, wherein the server provides multimedia communication between police personnel and one or more specialists relating to a test swipe analysis.

11. The tester of claim 1, comprising chemicals to detect one or more drug compounds.

12. The tester of claim 11, wherein each chemical causes each pad to display a color unique to an explosive compound.

13. The tester of claim 11, wherein the sequence of chemicals is deposited onto the pad at predetermined times or predetermined temperature range(s).

14. The tester of claim 11, wherein the sequence of chemicals is deposited onto the pad at predetermined hold time(s) each at predetermined temperature range(s).

15. The tester of claim 11, wherein each chemical deposited under predetermined time and temperature conditions reacts to a specific explosive or class of explosives to yield a specific color unique to the explosive.

16. The tester of claim 1, wherein the chemically treated pad comprises a substantially four-sided shape and adapted to receive a sequence of one or more chemicals to detect a drug compound.

17. The tester of claim 1, wherein the chemically treated area comprises a plurality of test regions.

18. The tester of claim 1, comprising a plurality of unique chemical solutions deposited on each test region.

19. A method for crime analysis, comprising:
capturing a background image of a test swipe;
applying one or more test chemicals to the test swipe with one or more processor controlled dispensers;
adjusting the temperature of the test swipe to a predetermined temperature range using a digitally-controlled heater;
upon contact with one or more chemicals in concert with heating and time profiles, displaying a sequence of a plurality of color reactions unique to multiple analytes, including explosives, drugs, or household chemicals;
capturing an in-situ image of the test swipe after the application of chemical at the predetermined temperature range;
subtracting the background image from the in-situ image;
generating a difference value from the two images; and
searching a known database to identify the substance.

20. The method of claim 19, comprising providing chemical scan data to one or more specialists over a wireless network to review the substance identification.

* * * * *